US008980835B2

(12) United States Patent
Okamoto et al.

(10) Patent No.: US 8,980,835 B2
(45) Date of Patent: Mar. 17, 2015

(54) CHEMICALLY MODIFIED WATER-SOLUBLE ELASTIN, MIXED GEL OF CHEMICALLY MODIFIED WATER-SOLUBLE ELASTIN AND COLLAGEN, AND PROCESS FOR PRODUCING SAME

(75) Inventors: Kouji Okamoto, Iizuka (JP); Hiroshi Yamada, Kitakyushu (JP); Yosuke Maegawa, Kitakyushu (JP); Ryota Watanabe, Kitakyushu (JP); Mitsuhiro Adachi, Kitakyushu (JP)

(73) Assignee: Kyushu Institute of Technology, Katakyushu-Shi (JP)

( * ) Notice: Subject to any disclaimer, the term of this patent is extended or adjusted under 35 U.S.C. 154(b) by 0 days.

(21) Appl. No.: 13/579,780

(22) PCT Filed: Feb. 16, 2011

(86) PCT No.: PCT/JP2011/053228
§ 371 (c)(1),
(2), (4) Date: Oct. 26, 2012

(87) PCT Pub. No.: WO2011/102363
PCT Pub. Date: Aug. 25, 2011

(65) Prior Publication Data
US 2013/0040891 A1 Feb. 14, 2013

(30) Foreign Application Priority Data
Feb. 19, 2010 (JP) .................. 2010-034149

(51) Int. Cl.
| | | |
|---|---|---|
| *C07K 14/78* | (2006.01) | |
| *A61K 8/65* | (2006.01) | |
| *A61P 9/00* | (2006.01) | |
| *A61K 47/42* | (2006.01) | |
| *A61L 27/22* | (2006.01) | |
| *A61L 27/52* | (2006.01) | |
| *A61L 27/24* | (2006.01) | |
| *A61L 27/50* | (2006.01) | |

(52) U.S. Cl.
CPC .............. *A61L 27/227* (2013.01); *A61L 27/52* (2013.01); *C07K 14/78* (2013.01); *A61L 27/24* (2013.01); *A61L 27/507* (2013.01)
USPC ........... 514/17.2; 514/1.1; 514/773; 514/785; 530/353

(58) Field of Classification Search
CPC ....... C08L 89/00; C08L 99/00; C08L 101/00; C08L 59/00; C08L 2203/02; A61K 47/42; A61K 9/70; A61K 38/02; A61K 41/00; A61K 41/0009; A61K 41/0019; A61K 45/06; A61K 2121/00; A61K 2201/10; A61L 27/227; A61L 27/24; A61L 27/27; A61L 27/22; A61L 27/26

See application file for complete search history.

(56) References Cited

U.S. PATENT DOCUMENTS

| 2004/0136977 A1 | 7/2004 | Miyamoto | |
| 2008/0096812 A1* | 4/2008 | Okamoto et al. | 514/12 |
| 2009/0124708 A1* | 5/2009 | Oliver et al. | 514/773 |

FOREIGN PATENT DOCUMENTS

| JP | 6-30616 B2 | 4/1994 |
| JP | 8-33661 A | 2/1996 |
| JP | 2007-45722 A | 2/2007 |
| JP | 2007-528918 A | 10/2007 |
| WO | WO 02/096978 A1 | 12/2002 |
| WO | WO 2005/084724 A1 | 9/2005 |

OTHER PUBLICATIONS

Ravi, Doctorate Dissertation, Georgia Institute of Technology (Dec. 2010) available at https://smartech.gatech.edu/bitstream/handle/1853/42728/Ravi_Swathi_201012_phd.pdf.*
Buttafoco et al., J Biomed Mater Res B Applied Biomater (2006) 77(2), 357-68.*
Trask et al., The Journal of Biological Chemistry (2000) 275, 24400-24406.*
Kagan et al., Biochimica et Biophysica Acta (1976) 434, 223-232.*
Fujimoto, M. et al., "Effect of heating process on the formation of nanoparticles of elastin model polypeptide, (GVGVP)251, by gamma-ray crosslinking", Polym. Bull., Dec. 17, 2009, pp. 707-716, vol. 64, No. 7.
Fujimoto, M. et al., "Preparation of alpha-elastin nanoparticles by gamma irradiation", Radiation Physics and Chemistry, 2009, pp. 1046-1048, vol. 78.
International Search Report issued in PCT/JP2011/053228, mailed Mar. 29, 2011.
Leach, J. B. et al., "Crosslinked α-elastin biomaterials: towards a processable elastin mimetic scaffold", Acta Biomaterialia, 2005, pp. 155-164, vol. 1.
Maegawa, Y. et al., "Characteristics of self-assembly of the chemically-modified soluble elastin and type I collagen in the coexisted state", Kitakyushu Iko Gakujutsusha Kyokaishi, Apr. 14, 2010, pp. 25-28, vol. 20.

* cited by examiner

*Primary Examiner* — Karlheinz R Skowronek
*Assistant Examiner* — Catherine Mader
(74) *Attorney, Agent, or Firm* — Birch, Stewart, Kolasch & Birch, LLP

(57) ABSTRACT

A chemically modified water-soluble elastin that is obtained by subjecting to N-acylating some or all of the primary amines and secondary amines contained in the molecule of a high molecular weight water-soluble elastin and coupling some or all of the carboxyl groups contained in the molecule with the amino group of an amino acid alkyl ester.
A chemically modified water-soluble elastin/collagen mixed gel obtained by mixing a collagen with a chemically modified water-soluble elastin that is obtained by subjecting to N-acylating some or all of the primary amines and secondary amines contained in the molecule of a high molecular weight water-soluble elastin and coupling some or all of the carboxyl groups contained in the molecule with the amino group of an amino acid alkyl ester.

14 Claims, 15 Drawing Sheets

CHEMICALLY MODIFIED WATER-SOLUBLE ELASTIN, MIXED GEL OF CHEMICALLY MODIFIED WATER-SOLUBLE ELASTIN AND COLLAGEN, AND PROCESS FOR PRODUCING SAME

TECHNICAL FIELD

The present invention relates to a chemically modified water-soluble elastin and a mixed gel of the chemically modified water-soluble elastin and a collagen that can be used in applications such as materials for artificial blood vessels, and a process for producing same.

BACKGROUND ART

An artificial blood vessel is used as a substitute for a blood vessel of a living organism when there is an injury or a disease of the circulatory system. As examples of artificial blood vessels that have recently been attracting attention, there are hybrid artificial blood vessels in which a collagen, a gelatin, an elastin, a fibronectin, etc. is incorporated into a synthetic polymer material and this is then seeded with cells. These hybrid artificial blood vessels have the problem that the cells are susceptible to being detached by rapid blood flow. Furthermore, there is a problem with biocompatibility since the material forming the substrate is a synthetic polymer, and when an artificial blood vessel having a diameter of 3 mm or less is prepared and grafted, it is necessary to continue to take an anticoagulant in order to prevent the intravascular lumen from being narrowed by a blood clot. Furthermore, there is the problem that, when this artificial blood vessel is grafted during a period of growth, it is necessary to graft an artificial blood vessel again by surgery accompanying the growth.

As the synthetic polymer used as the substrate for these hybrid artificial blood vessels, a stretched porous (expanded) polytetrafluoroethylene (e-PTFE) is currently dominant, and this polymer is excellent in terms of non-tackiness and flexibility, but has a problem with strength, and is used only for veins or small arteries (inner diameter 4 to 8 mm). As described above, since synthetic polymers have problems, biopolymers have been attracting attention as materials that can replace the synthetic polymers. Among biopolymers, collagens are present in large amounts in living organisms (occupying about ⅓ of the protein in a living organism) and have biocompatibility and cell-adhesion properties; preparation of an artificial blood vessel using a collagen has been attempted, but one formed from 100% collagen has a problem with strength.

Forming a medical material using a combination of a collagen and a water-soluble elastin is also known, as described later. Elastins are proteins that are present together with collagens in connective tissue such as the dermis of the skin, ligaments, tendons, and vascular wall of an animal and, in particular, a mammal. Elastins are usually present in a living organism as insoluble protein having a three-dimensional net structure. It is well known that hydrolyzing such an elastin with an acid or an alkali or treating it with an enzyme enables the above-mentioned water-soluble elastin to be obtained. Since a water-soluble elastin has the ability to retain a large amount of moisture, it is used as a cosmetic, in particular as a moisturizing agent, and also, together with a collagen, as a health food due to its cosmetic effects such as giving the skin elasticity.

Furthermore, with regard to the water-soluble elastin, a molding composition obtained by mixing a water-soluble elastin and a solubilized collagen (Patent Document 1) or provision of a collagen layer on an inner wall face of an artificial blood vessel substrate and crosslinking this with a water-soluble elastin using a crosslinking agent (Patent Document 2) have been proposed. Moreover, use of a mixture of a crosslinked elastin and a biopolymer such as a collagen as a medical material has been proposed (Patent Document 3). However, an artificial blood vessel, etc. that can withstand practical use has not been developed. Furthermore, the present inventors have proposed a method for obtaining a water-soluble elastin (Patent Document 4).

RELATED ART DOCUMENTS

Patent Documents

Patent Document 1: JP-B-6-30616 (JP-B denotes a Japanese examined patent application publication)
Patent Document 2: JP-A-8-33661 (JP-A denotes a Japanese unexamined patent application publication)
Patent Document 3: International Patent Application WO 2002-96978
Patent Document 4: JP-A-2007-45722

SUMMARY OF THE INVENTION

Problems to be Solved by the Invention

It is an object of the present invention to provide a medical material such as an artificial blood vessel having excellent biocompatibility and sufficient strength, elasticity, and extensibility using a water-soluble elastin and a collagen.

Means for Solving the Problems

The above-mentioned object has been attained by embodiments of the present invention as described below.

One embodiment of the present invention is a chemically modified water-soluble elastin that is obtained by subjecting to N-acylating some or all of the primary amines and secondary amines contained in the molecule of a high molecular weight water-soluble elastin and coupling some or all of the carboxyl groups contained in the molecule with the amino group of an amino acid alkyl ester. As the N-acylation, there are N-formylation, N-acetylation, N-benzoylation, etc., and N-acetylation is preferable. Furthermore, the N-acylation may employ a urethane type or an alkyl type. The amino acid used in acid amidation of the carboxyl groups of the elastin using an amino acid alkyl ester is selected from about 20 types, such as glycine, valine, phenylalanine, etc., that form proteins. In the present invention, the term 'high molecular weight water-soluble elastin' means one having a molecular weight of at least about 10,000, and preferably about 30,000 to 300,000.

Another embodiment of the present invention is a chemically modified water-soluble elastin/collagen mixed gel obtained by mixing a collagen with a chemically modified water-soluble elastin that is obtained by subjecting to N-acylating some or all of the primary amines and secondary amines contained in the molecule of a high molecular weight water-soluble elastin and coupling some or all of the carboxyl groups contained in the molecule with the amino group of an amino acid alkyl ester. In this embodiment a chemically modified water-soluble elastin/collagen mixed gel obtained by mixing the chemically modified water-soluble elastin with substantially the same weight of a collagen is preferable. Furthermore, a chemically modified water-soluble elastin/collagen mixed gel obtained by mixing the chemically modified water-soluble elastin with a smaller amount or a larger amount of a collagen is also preferable. The term 'substantially the same weight' means that the ratio by weight of the chemically modified water-soluble elastin and the collagen is within 95 to 105 wt %.

Yet another embodiment of the present invention is a process for producing the chemically modified water-soluble elastin/collagen mixed gel, and is a process for producing a chemically modified water-soluble elastin/collagen mixed gel comprising (1) a step of subjecting to N-acylating some or all of the primary amines and secondary amines contained in the molecule of a high molecular weight water-soluble elastin, (2) a step of coupling some or all of the carboxyl groups contained in the molecule of the high molecular weight water-soluble elastin with the amino group of an amino acid lower alkyl ester, and (3) a step of preparing a mixed gel by mixing in a solution state the chemically modified water-soluble elastin obtained via steps (1) and (2) with a collagen. In this embodiment also, a process involving mixing the chemically modified water-soluble elastin with substantially the same weight of a collagen is preferable. Furthermore, a process involving mixing the chemically modified water-soluble elastin with a smaller amount or a larger amount of a collagen is also preferable.

Yet another embodiment of the present invention is a process for producing a chemically modified water-soluble elastin/collagen mixed gel, the process comprising (1) a step of subjecting to N-acylating some or all of the primary amines and secondary amines contained in the molecule of a high molecular weight water-soluble elastin, (2) a step of coupling some or all of the carboxyl groups contained in the molecule of the high molecular weight water-soluble elastin with the amino group of an amino acid lower alkyl ester, (3) a step of preparing a mixed gel by mixing in a solution state the chemically modified water-soluble elastin obtained via steps (1) and (2) with a collagen, and (4) a step of irradiating the mixed gel obtained in (3) with radiation. In this embodiment also, a process involving mixing the chemically modified water-soluble elastin with substantially the same weight of a collagen is preferable. Furthermore, a process involving mixing the chemically modified water-soluble elastin with a smaller amount or a larger amount of a collagen is also preferable.

Yet another embodiment of the present invention is use as a medical material of the above-mentioned chemically modified water-soluble elastin. Furthermore, yet another embodiment of the present invention is use as a medical material of the chemically modified water-soluble elastin/collagen mixed gel or a chemically modified water-soluble elastin/collagen mixed gel produced by the above-mentioned production process. Here, the medical material includes an artificial blood vessel material, etc.

MODES FOR CARRYING OUT THE INVENTION

Figure 1:
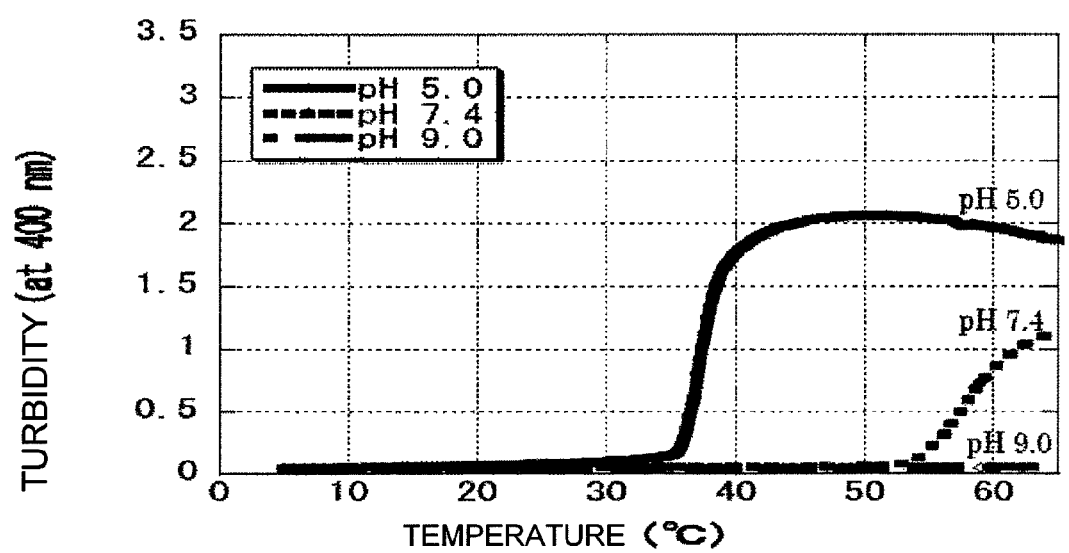
FIG. 1 is a curves (turbidity curves) showing the relationship between turbidity and temperature at pHs of 5.0, 7.4, and 9.0 of a non-modified water-soluble elastin (Ela).

When the water-soluble elastin of the present invention is derived from a mammal or a bird, it is a high molecular weight water-soluble elastin having a molecular weight of about 10,000 to 300,000, and preferably about 30,000 to 300,000, in which about 78% to 85% of the amino acids forming the elastin comprise proline, glycine, alanine, and valine, about 2% to 4% comprise aspartic acid and glutamic acid, about 1% to 2% comprise lysine, histidine, and arginine, and about 0.1% to 0.4% comprise desmosine and isodesmosine. Furthermore, when the water-soluble elastin of the present invention is derived from a fish, it is a high molecular weight water-soluble elastin having a molecular weight of about 10,000 to 300,000, and preferably about 30,000 to 300,000, in which about 67% to 77% of the amino acids forming the elastin comprise proline, glycine, alanine, and valine, about 4% to 6% comprise aspartic acid and glutamic acid, about 2% to 4% comprise lysine, histidine, and arginine, and about 0.1% to 0.4% comprise desmosine and isodesmosine.

The chemically modified water-soluble elastin of the present invention is a chemically modified water-soluble elastin obtained by subjecting some or all of the primary amines and secondary amines contained in the molecule of a high molecular weight water-soluble elastin to N-acylation and coupling some or all of the carboxyl groups contained in the molecule with the amino group of an amino acid alkyl ester. As the N-acylation, there are N-formylation, N-acetylation, N-benzoylation, etc., and N-acetylation is preferable. Furthermore, the N-acylation may employ a urethane type or an alkyl type. The amino acid used in acid amidation of the carboxyl group of the elastin using an amino acid alkyl ester may be any of about 20 types, such as glycine, valine, phenylalanine, etc., that form proteins.

The chemically modified water-soluble elastin/collagen mixed gel of another embodiment of the present invention is produced by first a step of subjecting some or all of the primary amines and secondary amines contained in the molecule of a high molecular weight water-soluble elastin so obtained to N-acylation (first step), subsequently a step of coupling some or all of the carboxyl groups contained in the molecule of the N-acylated water-soluble elastin with the amino group of an amino acid lower alkyl ester to thus carry out chemical modification (second step), and after that a step of mixing in a solution state the chemically modified water-soluble elastin so obtained with substantially the same weight, or a smaller or larger amount, of a collagen to prepare a mixed gel (third step).

An irradiated chemically modified water-soluble elastin/collagen mixed gel, which is another embodiment of the present invention, is obtained by first subjecting some or all of the primary amines and secondary amines contained in the molecule of a high molecular weight water-soluble elastin to N-acylation (first step), subsequently coupling some or all of the carboxyl groups contained in the molecule of the N-acylated water-soluble elastin so obtained with the amino group of an amino acid lower alkyl ester to thus carry out chemical modification (second step), furthermore mixing in a solution state the chemically modified water-soluble elastin obtained via the first step and the second step with a collagen to thus prepare a mixed gel (third step), and then irradiating the mixed gel so obtained with radiation (fourth step). In this embodiment also, production is by a step of mixing in a solution state the chemically modified water-soluble elastin with substantially the same weight, or a smaller or larger amount, of a collagen to thus prepare a mixed gel. The ratio (chemically modified water-soluble elastin/collagen) by weight of the chemically modified water-soluble elastin and the collagen is preferably 1/200 to 200/1, more preferably 1/100 to 50/1, yet more preferably 1/50 to 5/1, and particularly preferably 1/3 to 3/1.

For example, when an artificial ligament, artificial skin, an artificial tendon, an artificial blood vessel, etc. is prepared as a body tissue substitute using the chemically modified water-soluble elastin/collagen mixed gel of the present invention, the ratio by weight is preferably 1/50 to 5/1, and when an artificial fiber, an artificial anti-adhesion membrane, an artificial surgical suture, an artificial membrane, etc., which is not a body tissue substitute, is prepared, the wider the range of elastin weight/collagen weight the better it is, and the ratio by weight is preferably 1/100 to 50/1; when it is applied to for example a non-biological synthetic fiber, synthetic membrane, etc., an even wider range of elastin weight/collagen weight is better, and the ratio by weight is preferably 1/200 to 200/1.

In the present invention, a chemically modified water-soluble elastin is obtained by subjecting amino groups, etc. of the N-terminus of a water-soluble elastin and of an amino acid residue side chain of lysine, arginine, etc. to N-acylation and subsequently coupling carboxyl groups, etc. of the C-terminus and of an amino acid residue side chain of aspartic acid, glutamic acid, etc. with the amino group of an amino acid alkyl ester. Due to the amino group, etc. and the carboxyl group, etc. being protected by chemical modification, charge of the elastin disappears, as a result hydrophobic interaction between elastin molecules increases, and the chemically modified water-soluble elastin thus obtained can be expected to have high self-assembling properties compared with a non-modified elastin.

Various methods and means for obtaining a water-soluble elastin have been proposed. The methods below, which have been proposed by the present inventors, are preferable (ref. Patent Document 4).

The first method produces a water-soluble elastin by removing collagen and other unwanted proteins from an animal body tissue to obtain an insoluble elastin and then immersing and dissolving this insoluble elastin in a solubilizing liquid such as oxalic acid or sodium hydroxide. Removal of collagen and other unwanted proteins is preferably carried out by immersing the animal body tissue in an alkaline solution containing at least any one of sodium hydroxide, potassium hydroxide, calcium hydroxide, and barium hydroxide at a temperature of 90° C. to 105° C. for 5 to 60 minutes, and preferably 10 to 20 minutes, the total amount of sodium hydroxide, potassium hydroxide, calcium hydroxide, and barium hydroxide added to the alkaline solution being 0.05 to 0.5 mol per L, and preferably 0.05 to 0.3 mol per L. Furthermore, when removing collagen and other unwanted proteins, prior to treatment with the alkaline solution, it is preferable to carry out an immersion treatment (pretreatment) of immersing the animal body tissue in a salt solution containing at least any one of sodium chloride, potassium chloride, calcium chloride, and barium chloride.

The animal body tissue is not particularly limited, but from the viewpoint of the elastin content being high is preferably nuchal ligament or aortic blood vessel obtained from a mammal such as a pig, a horse, a cow, or a sheep. It is also possible to use the aortic blood vessel of a bird or the aortic bulb (heart) of a fish, which has a high elastin content. The animal body tissue may first be homogenized using a homogenizer. Homogenization may be carried out using a mixer, a meat grinder, etc. so that the animal body tissue may be finely fragmented, and is preferably carried out using a tool that can fragment it into pieces smaller than 3 mm square, and more preferably into a paste. The smaller the fragmented particles of the animal body tissue, the higher the efficiency of removing collagen and other unwanted protein, this being preferable. The homogenized animal body tissue may be subjected to a delipidation treatment by for example boiling it in hot water or a hot diluted aqueous alkaline solution or treating with an organic solvent.

As the solubilizing liquid, an acidic solution comprising at least any one of oxalic acid, formic acid, acetic acid, succinic acid, malic acid, tartaric acid, citric acid, benzoic acid, a betaine, difluoroacetic acid, trifluoroacetic acid, phosphoric acid, sulfamic acid, perchloric acid, and trichloroacetic acid is used. The total amount of acids of this acidic solution is 0.05 to 5 mol per L, and preferably 0.1 to 2 mol per L, and the liquid temperature is preferably 90° C. to 105° C.

The solubilizing liquid may be an alkaline solution comprising at least any one of sodium hydroxide, potassium hydroxide, calcium hydroxide, and barium hydroxide. The total amount of sodium hydroxide, potassium hydroxide, calcium hydroxide, and barium hydroxide added to this alkaline solution is 0.05 to 5 mol per L, and preferably 0.05 to 2 mol per L, and the liquid temperature of the alkaline solution is preferably 90° C. to 105° C.

The second method is a method for producing an water-soluble elastin by carrying out in sequence a pretreatment step comprising at least one of an unwanted animal body tissue parts removal treatment, an animal body tissue fragmentation treatment, an animal body tissue delipidation treatment, and a salt treatment, an alkali extraction step of immersing the pretreated animal body tissue in an alkaline solution and separating collagen and other unwanted proteins by filtration, a filtrate recovery step of obtaining a filtrate containing a water-soluble elastin by filtration by repeating a predetermined number of times an alkali dissolution step of dissolving the residue by means of an alkali after the alkali extraction step, and a water-soluble elastin formation step of producing a water-soluble elastin from the filtrate. As the alkali used in the alkali dissolution step, any one of sodium hydroxide, potassium hydroxide, calcium hydroxide, and barium hydroxide, or a mixture thereof, is preferable.

Unlike the above-mentioned first method in which collagen and other unwanted proteins are removed from tissue to obtain an insoluble elastin and subsequently this insoluble elastin is solubilized to obtain a water-soluble elastin, this procedure is a method of directly obtaining a water-soluble elastin without obtaining an insoluble elastin from the tissue. That is, it is a method of obtaining a water-soluble elastin in which an animal body tissue that has been fragmented, delipidated, and treated with a salt is immersed in a 0.05 to 0.5 mol, and preferably 0.05 to 0.3 mol, per L alkaline solution at 90° C. to 105° C. for 5 to 60 min, and preferably 10 to 20 min to obtain a treated tissue from which collagen and unwanted protein other than elastin have been removed, and subsequently this treated tissue is immersed in a 0.05 to 5 mol, and preferably 0.05 to 2 mol (the concentration of the alkaline solution being higher), per L alkaline solution at 90° C. to 105° C. for 5 to 420 min, and preferably 10 to 240 min (the time being longer), thus carrying out dissolution.

With regard to the water-soluble elastin obtained by the first or second method as described above, the aqueous solution containing the water-soluble elastin is neutralized, and subsequently the neutralized solution is subjected to a dialysis treatment or a membrane treatment using a nanofiltration (NF) membrane, etc. to thus carry out desalting and remove low molecular weight components, thereby giving the high molecular weight water-soluble elastin used in the present invention.

As the collagen used in the present invention, any collagen known as being for medical use may be used. Collagen normally suitable for medical use is usually obtained, as a viscous collagen solution or a solid formed by drying this solution, by a method in which it is extracted, mainly from animals as a source, by means of an enzyme under acidic, alkaline, or neutral conditions. Furthermore, antigenicity-exhibiting sites may be removed by further subjecting it to a pepsin treatment, thus giving a collagen (atelocollagen) more suitable for a medical substrate that has no antigenicity when grafted within the body or on the body surface. Representative examples of collagens used in the present invention include solubilized collagens such as acid-solubilized collagen, alkali-solubilized collagen, enzyme-solubilized collagen, and neutral-solubilized collagen, and in particular an atelocollagen, which has been subjected to a treatment involving removing telopeptides, which are epitopes of collagen, at the same time as the solubilization treatment.

When producing the chemically modified water-soluble elastin/collagen mixed gel of the present invention, first, some or all of the primary amines and secondary amines contained in the molecule of a high molecular weight water-soluble elastin are subjected to N-acylation, and preferably N-acetylation, thus giving an N-acetylated water-soluble elastin. Among amino acid residues forming elastin, as amino acids having a reactive primary amine or secondary amine (basic amino acid) lysine, arginine, and histidine can be cited, and as a primary amine contained in the high molecular weight water-soluble elastin a terminal amino group is also included.

In the present invention, some or all of the primary amines and secondary amines contained in the molecule of a high molecular weight water-soluble elastin are preferably N-acetylated by an acetylation reagent such as acetic anhydride, and the degree of N-acetylation is preferably at least 95% when expressed as a degree of modification represented by the equation below.

$$\text{Degree of modification (\%)} = (1 - B/A) \times 100$$

A is a value obtained by subtracting the average value of the absorbance of a blank from the average value of the absorbance (wavelength 345 nm) of a water-soluble elastin. B is a value obtained by subtracting the average value of the absorbance of a blank from the average value of the absorbance (wavelength 345 nm) of an N-acetylated water-soluble elastin.

In the present invention, some or all of the carboxyl groups contained in the N-acylated, and preferably N-acetylated, water-soluble elastin molecules so obtained are subsequently chemically modified by coupling them with the amino group of an amino acid alkyl ester, thus giving a chemically modified water-soluble elastin. In the present invention, a lower alkyl ester having 1 to 4 carbons is preferable, and a methyl ester is particularly preferable. It is also possible to use a benzyl ester or the like. Among amino acid residues forming elastin, as amino acids having a carboxyl group (acidic amino acid) there are aspartic acid and glutamic acid, and as carboxyl groups contained in the high molecular weight water-soluble elastin molecule a terminal carboxyl group is also included.

In the present invention, substantially all of the carboxyl groups contained in the N-acylated, and preferably N-acetylated, water-soluble elastin molecule are preferably coupled with the amino group of an amino acid alkyl ester. When carrying out a coupling reaction, a coupling agent or condensing agent such as a carbodiimide is conveniently used.

Subsequently, in the present invention, an aqueous solution of the chemically modified water-soluble elastin obtained as above and an aqueous solution of the above-mentioned collagen are separately prepared, and a mixed gel is prepared by mixing them in an aqueous solution state with substantially the same weight content of each or in an aqueous solution state in which the amount of the chemically modified water-soluble elastin is increased or decreased relative to the collagen. The chemically modified water-soluble elastin/collagen mixed gel of the present invention is obtained by such a method. The mixed gel thus obtained can be used as a substrate for a medical material such as an artificial blood vessel as it is, or after subjecting it to appropriate processing.

In another embodiment of the present invention, the chemically modified water-soluble elastin/collagen mixed gel obtained as above is irradiated with radiation such as an electron bean or γ rays in a swollen state as a solution or in a dry state, thus giving an irradiated chemically modified water-soluble elastin/collagen mixed gel. As the radiation, γ rays are preferable, and the radiation intensity required to increase the Young's modulus of the mixed gel by preferably at least twice is applied.

In accordance with irradiation with γ rays, etc., the mixed gel is sterilized and crosslinked, thus further increasing the strength of the material. Irradiation conditions are not particularly limited, but for example in the case of Co-60 γ rays, it is desirable to apply them at 20° C. to 50° C., and preferably 30° C. to 40° C., at about 0.5 to 50 kGy, and preferably about 5 to 40 kGy.

Since a material obtained from the chemically modified water-soluble elastin/collagen mixed gel of the present invention has greatly improved strength, resilience, and extensibility compared with an elastin or a collagen on its own or a mixture thereof, there is a high possibility of it being used as a medical material such as an artificial blood vessel. When an amino acid having high hydrophobicity is used as the amino acid used four chemical modification or when a peptide having high hydrophobicity is used for chemical modification, an artificial blood vessel material, etc. having the same level of stress as porcine or canine aorta or a higher level of strength, resilience, and extensibility may be prepared.

Examples

The present invention is explained in detail below by reference to Examples. The various types of measurement methods were as follows.

(Degree of Modification by N-Acetylation)

The degree of modification by N-acetylation was calculated after measurement by a TNBS (2,4,6-trinitrobenzenesulfonic acid) method as follows. 1 mL each of a 4% sodium bicarbonate solution and a 0.1% TNBS aqueous solution were added to a 1 mg/mL N-acetylated water-soluble elastin (N-Ac-Ela) aqueous solution. One containing only 1 mL each of a 4% sodium bicarbonate solution and a 0.1% TNBS aqueous solution was used as a blank (n=3). The solutions so prepared were shielded from light using aluminum foil, and a reaction was carried out at 40° C. for 2 hours. After the reaction was complete, 1 mL of 10% SDS and 0.5 mL of 1N HCl were added to 0.17 mL of the solutions that were prepared, and the absorbance at 345 nm was measured. The degree of modification was determined from the equation below.

In the equation, A is obtained by subtracting the average value of the absorbance of the blanks from the average value of the absorbance of the elastin aqueous solutions, and B is obtained by subtracting the average value of the absorbance of the blanks from the average value of the absorbance of the N-Ac-Ela aqueous solutions. The degree of modification is expressed as degree of modification (%)=(1−B/A)×100.

(Turbidity Measurement)

Water-soluble elastin (Ela), three types of chemically modified water-soluble elastins (Cm-Ela), and a type I collagen (Col) were each dissolved in PBS (phosphate buffered saline, pH 7.4) or a solution with a pH of 5.0, 7.4, or 9.0. The turbidity of these solutions of Ela on its own, 3 types of Cm-Ela's on their own, Col on its own, an Ela and Col mixed state, and 3 types of Cm-Ela/Col mixed states were measured at a wavelength of 400 nm in a temperature range of 5° C. to 65° C. with a temperature increase of 0.5° C./min under a flow of nitrogen. The solvent used was ultrapure water or PBS while taking into consideration the physiological conditions, and the measurement equipment used was a Peltier type temperature controller-equipped spectrophotometer (Ubest-50, JASCO Corporation).

(Preparation of Porcine Water-Soluble Elastin)

1) Isolation of Porcine Insoluble Elastin

In accordance with the procedure below, NaCl-soluble and NaOH-soluble proteins such as collagen and unwanted proteins other than elastins were extracted and removed from porcine aorta delipidated tissue.

Porcine aorta delipidated tissue (body tissue) was used; as a pretreatment, a treatment involving removing unwanted portions by scraping off portions having a low elastin content such as attached fat or muscle using a knife, etc. was carried out, and subsequently a fragmentation treatment was carried out by homogenizing the body tissue using a homogenizer. A delipidation treatment of treating the homogenized body tissue with hot water, a hot diluted aqueous alkaline solution, or an organic solvent such as acetone was carried out, and the tissue was then dried. About 10 times by volume of the weight of the delipidated and dried tissue of 1M sodium chloride was added, and the mixture was stirred at room temperature for 1 hour, thus extracting and removing unwanted NaCl-soluble proteins. After this procedure was repeated five times, the tissue was washed with distilled water and drained by centrifugation (3,000 rpm, 5 min).

A step of adding about 10 times by volume (10 mL per g of weight) relative to the weight of the delipidated and salt-treated tissue obtained above of a 0.1 N sodium hydroxide aqueous solution, stirring the mixture at 100° C. for 15 min, and removing collagen and unwanted protein other than elastin was carried out. The resulting tissue and the alkaline solution were then separated. This procedure was repeated until the total amount by mass of proteins contained in the separated alkaline solution when measured for example by a burette method became no greater than 0.1 mg/mL. Subsequently, cooling and washing by centrifugation (5,000 rpm, 20 min) were carried out, and the residue was dried, thus giving an insoluble elastin.

2) Preparation of High Molecular Weight Porcine Water-Soluble Elastin 10 times by volume of the dry weight of the porcine insoluble elastin of 0.5 N sodium hydroxide was added, and the mixture was stirred at 100° C. for 30 min. After the reaction, the solution was quickly cooled with ice and neutralized with acetic acid or hydrochloric acid. Subsequently, dialysis was carried out using a dialysis membrane for separating material having a molecular weight of 6,000 to 8,000 or over for 1 week. Subsequently, the sample was lyophilized, thus giving a high molecular weight porcine water-soluble elastin.

(Preparation of Chemically Modified Water-Soluble Elastin)

Chemical modification of the high molecular weight porcine water-soluble elastin was carried out by N-acetylation and coupling with an O-amino acid methyl ester.

1) Preparation of N-Acetylated Water-Soluble Elastin

Pyridine (100 eq) and acetic anhydride (100 eq) were added to a solution of the porcine water-soluble elastin obtained above in a small amount of trifluoroethanol (TFE) and stirred overnight. After it was confirmed by a ninhydrin test that acetylation had proceeded quantitatively, the reaction mixture was evacuated and concentrated using an evaporator. This N-acetylation was repeated several times until the degree of modification of amino groups, etc. became at least 95% by the TNBS method. Subsequently, this solution was subjected to dialysis for 1 week to thus remove the solvent and unreacted reagent, and lyophilized, thus giving an N-acetylated water-soluble elastin.

In the present invention, the number of molar equivalents (eq) of a reagent is expressed on the basis of the number of moles (1 mole equivalent) of starting material used, determined from the average molecular weight of the N-acetylated water-soluble elastin. This also applies to the 'Brief Description of Drawings' section.

2) Coupling Reaction of Amino Acid Methyl Ester

A water-soluble carbodiimide (WSCI) was added to solutions of the N-acetylated water-soluble elastin (N-Ac-Ela) obtained above in a small amount of dimethylformamide (DMF). After stirring for 15 min., a small amount of DMF solution in which each of three types of amino acid methyl esters, that is, glycine (G) methyl ester (H-G-OMe), valine (V) methyl ester (H-V-OMe), and phenylalanine (F) methyl ester (H-F-OMe), and triethylamine were dissolved was added. After stirring for 24 hr, these solutions were subjected to dialysis for 1 week to remove solvent, unreacted reagent, etc., and lyophilized, thus giving three types of chemically modified water-soluble elastins, that is, N-acetyl-O-G-methyl ester water-soluble elastin (Cm(G)-Ela), N-acetyl-O-V-methyl ester water-soluble elastin (Cm(V)-Ela), and N-acetyl-O-F-methyl ester water-soluble elastin (Cm(F)-Ela).

Figure 2:
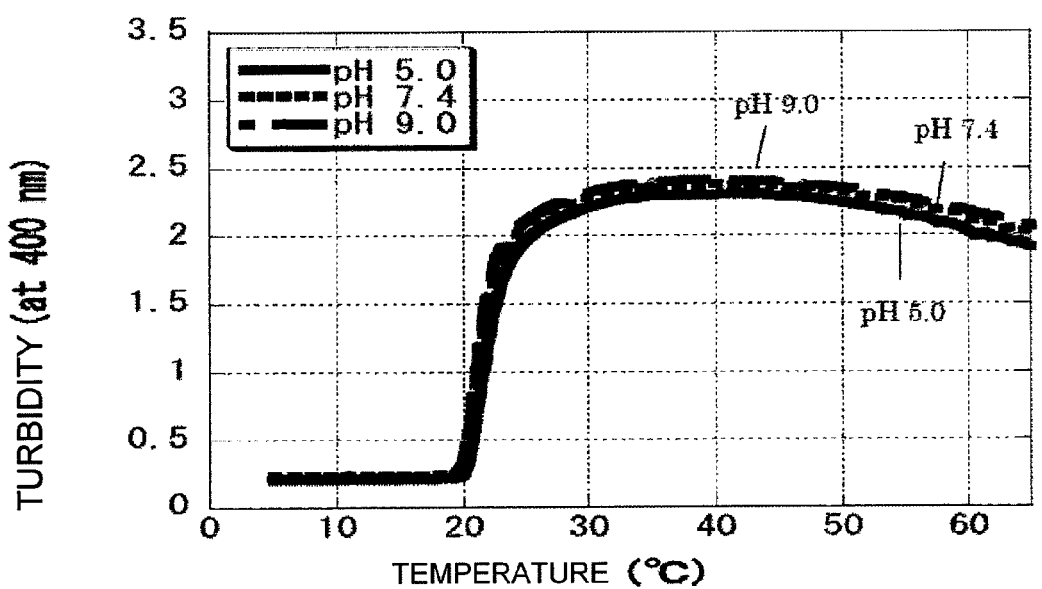
FIG. 2 is a turbidity curves at pHs of 5.0, 7.4, and 9.0 of N-acetyl-O-G-methyl ester water-soluble elastin (Cm(G)-Ela) prepared by coupling N-acetyl water-soluble elastin (N-Ac-Ela) and glycine (G) methyl ester using WSCI (100 eq).
Figure 3:
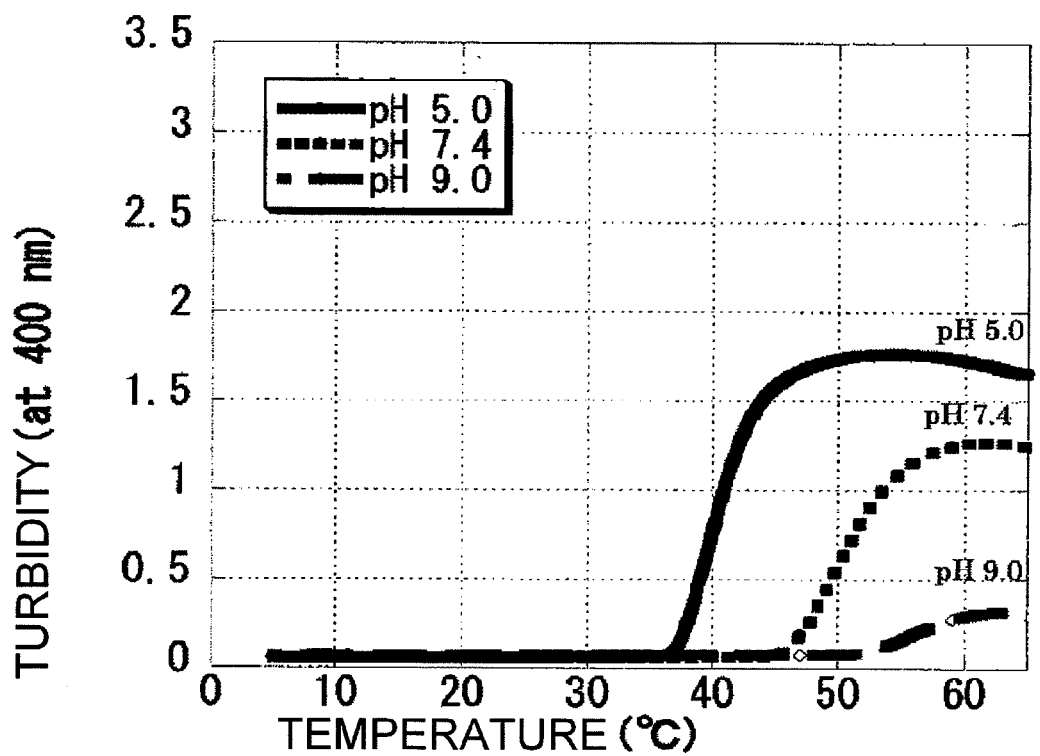
FIG. 3 is a turbidity curves at pHs of 5.0, 7.4, and 9.0 of N-acetyl-O-G-methyl ester water-soluble elastin (Cm(G)-Ela) prepared by coupling N-Ac-Ela and glycine (G) methyl ester using WSCI (10 eq).
Figure 4:
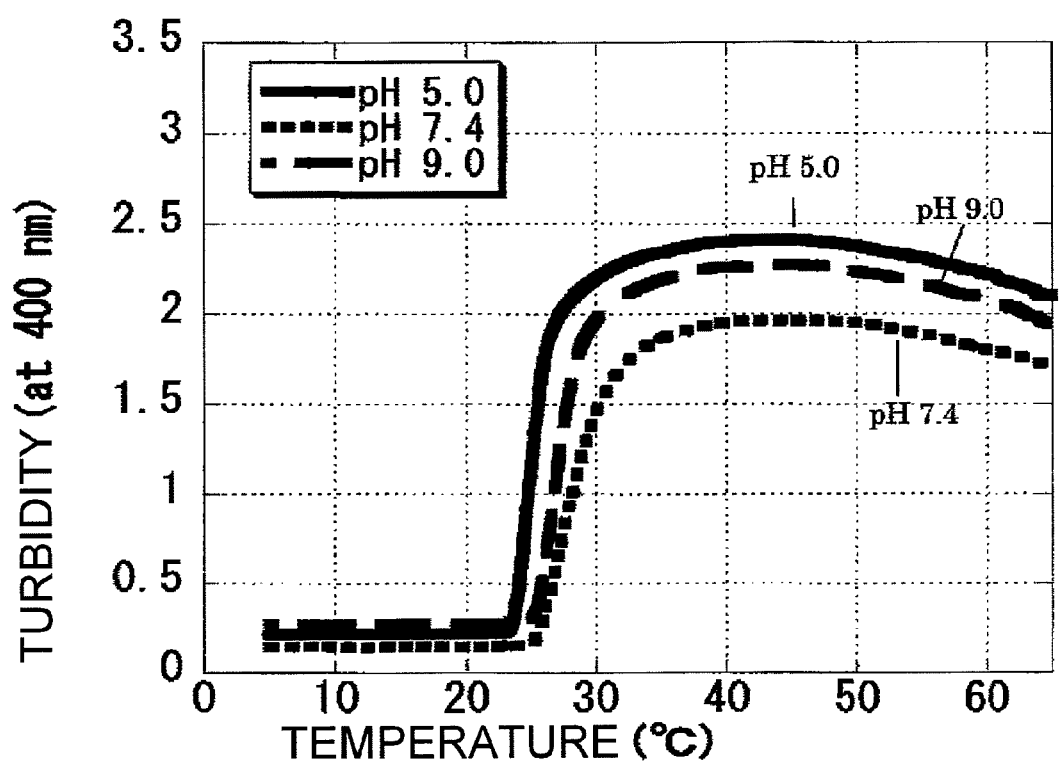
FIG. 4 is a turbidity curves at pHs of 5.0, 7.4, and 9.0 of N-acetyl-O-G-methyl ester water-soluble elastin (Cm(G)-Ela) prepared by coupling N-Ac-Ela and glycine (G) methyl ester using WSCI (50 eq).

The results with non-modified Ela are shown in FIG. 1, and the results of coupling N-Ac-Ela with an amino acid methyl ester using a WSCI are shown in FIGS. 2 to 4. FIG. 1 shows curves (turbidity curves) showing the relationship between turbidity and temperature of the non-modified Ela at pHs of 5.0, 7.4, and 9.0, and FIG. 2 shows turbidity curves at pHs of 5.0, 7.4, and 9.0 of Cm(G)-Ela formed by coupling N-Ac-Ela and glycine (G) methyl ester using a WSCI (100 eq). From FIG. 1, Ela did not self-assemble at 37° C. and a pH of 7.4, which are physiological conditions. The reason why no self assembly occurred is because the isoelectric point of Ela is on the acidic side (around pH 5.5). In order to bring the isoelectric point to around pH 7.4, in the present invention, the amino groups are N-acetylated, and the carboxyl groups are chemically modified by coupling with a amino acid methyl ester.

As a result, as shown in FIG. 2 the temperature at which the chemically modified water-soluble elastin (Cm-Ela) starts to self-assemble shifted toward the low temperature side relative to the temperature at which Ela starts to self-assemble, and sufficient turbidity intensity is exhibited under physiological conditions (around pH 7.4). It can be seen that since the turbidity intensity increased and substantially the same turbidity curve was obtained at different pHs, the degree of modification of the carboxyl group, etc. by coupling with an amino acid methyl ester was substantially complete.

FIG. 3 and FIG. 4 are graphs showing the relationship between the turbidity curve and the amount of coupling agent (WSCI) added when coupling N-Ac-Ela and an amino acid methyl ester. FIG. 3 is a case when the amount of WSCI was 10 eq, and FIG. 4 is a case when the amount of WSCI was 50 eq. It can be seen that the amount of WSCI added greatly affected the degree of modification, but taking into consideration the amount of WSCI being 100 eq in FIG. 2, the coupling reaction proceeded substantially completely with the use of 100 eq.

Figure 5:
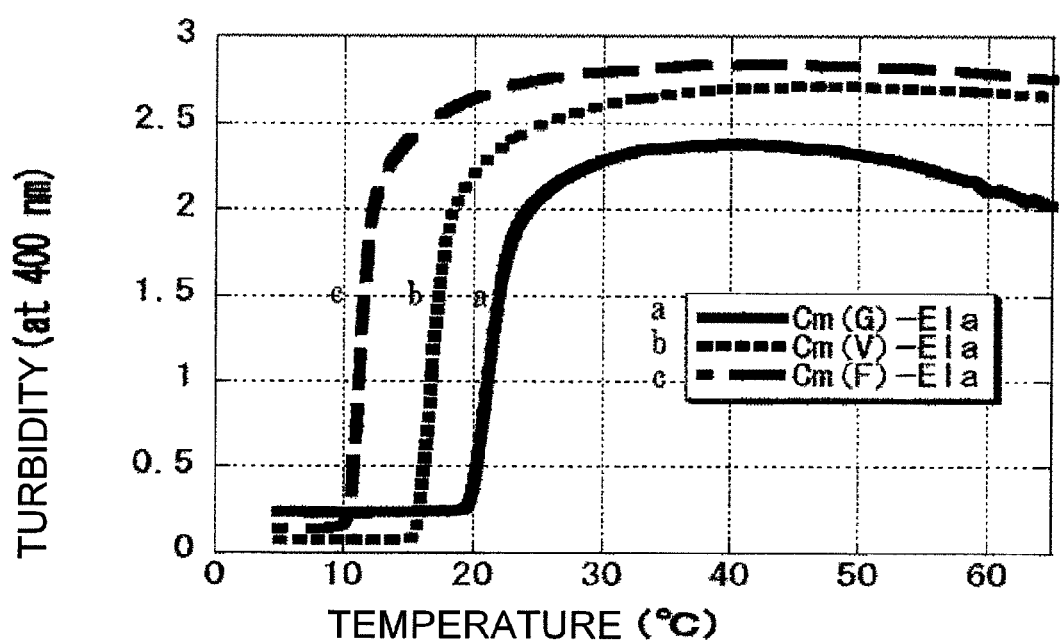
FIG. 5 is a turbidity curves at a pH of 7.4 of three different types of chemically modified water-soluble elastins (Cm-Ela), that is, N-acetyl-O-G-methyl ester water-soluble elastin (Cm(G)-Ela), N-acetyl-O-V-methyl ester water-soluble elastin (Cm(V)-Ela), and N-acetyl-O-F-methyl ester water-soluble elastin (Cm(F)-Ela).

FIG. 5 shows turbidity curves of three different types of chemically modified water-soluble elastins, that is, Cm(G)-Ela, Cm(V)-Ela, and Cm(F)-Ela. It can be seen that the higher the hydrophobicity of the glycine (G), valine (V), and phenylalanine (F) amino acids that were used, the lower the temperature at which self assembly started, and the higher the turbidity intensity. This suggests that self assembly of Ela is promoted when the hydrophobicity of the molecule is higher.

(Preparation of Water-Soluble Elastin/Collagen Mixed Gel and Chemically Modified Water-Soluble Elastin/Collagen Mixed Gel)

A total amount of 2 mL of a solution was prepared so that the ratio of collagen and water-soluble elastin or the ratio of collagen and chemically modified water-soluble elastin was 1.5 mg/mL:1.5 mg/mL, and the ratio of collagen and chemically modified water-soluble elastin was 1.5 mg/mL:4.5 mg/mL. The solvent used was PBS (pH 7.4). The solution was allowed to stand at 37° C. for 1 hour, thus carrying out gelling. Subsequently, the gel was dried and vitrified, then mixed with 2 mL of PBS (pH 7.4) and allowed to stand for 48 hours to thus make it swell, thereby giving the chemically modified water-soluble elastin/collagen mixed gel of the present invention.

(Measurement of Various Performance Characteristics of Chemically Modified Water-Soluble Elastin/Collagen Mixed Gel)

(Turbidity Curve)

Figure 6:
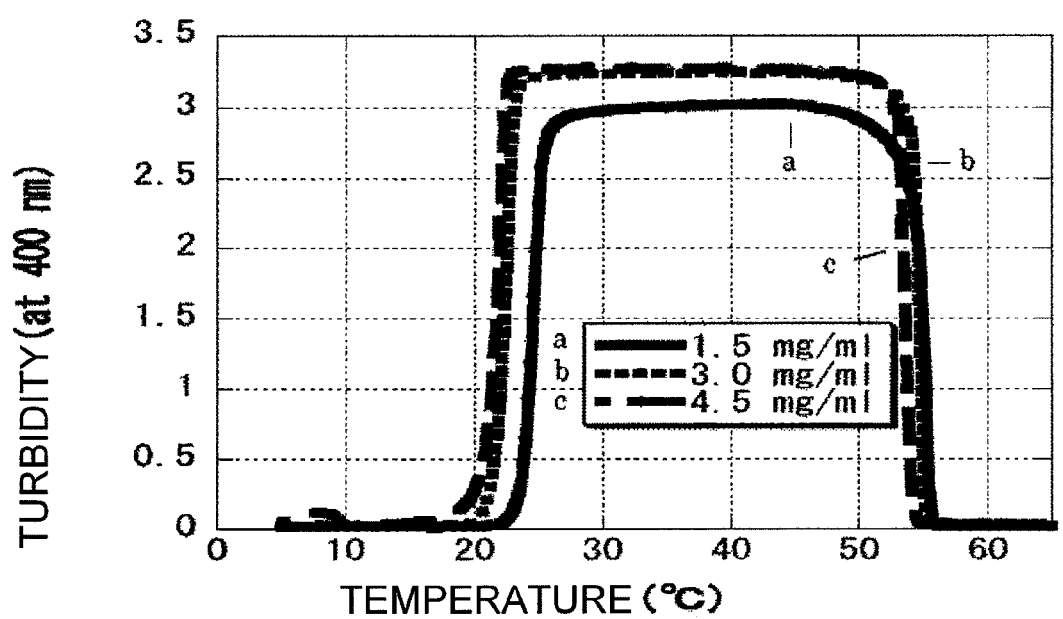
FIG. 6 is a turbidity curves at a pH of 7.4 of a collagen (Col) on its own at concentrations of 1.5 mg/mL, 3.0 mg/mL, and 4.5 mg/mL.
Figure 7:
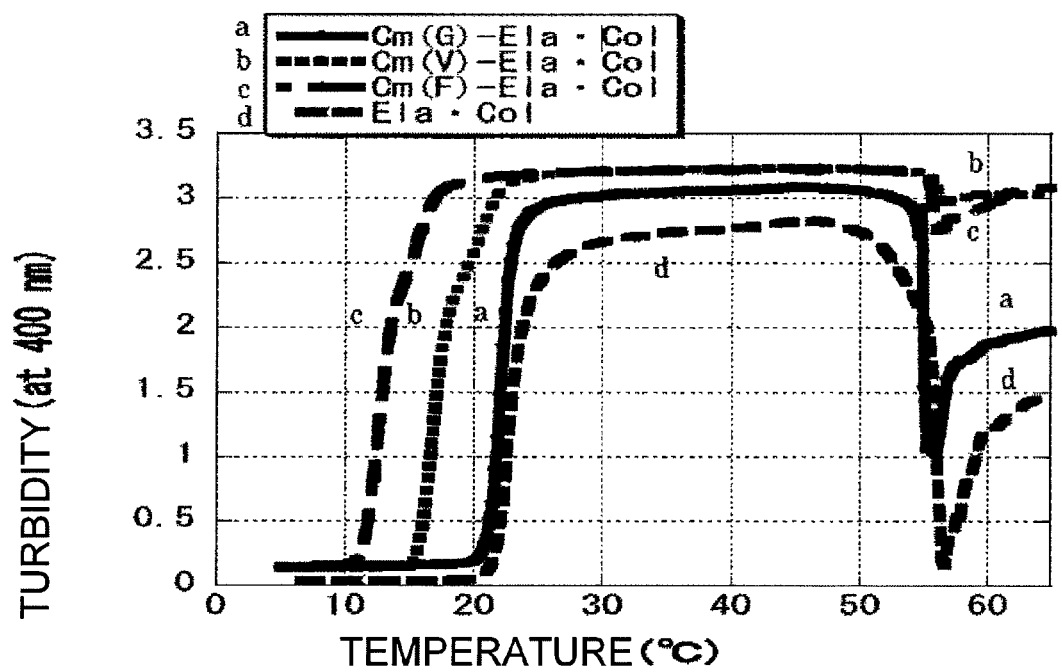
FIG. 7 is a turbidity curves at a pH of 7.4 of an Ela/Col mixed solution (mixing ratio 1.5 mg/mL:1.5 mg/mL), a Cm(G)-Ela/Col mixed solution (mixing ratio 1.5 mg/mL:1.5 mg/mL), a Cm(V)-Ela/Col mixed solution (mixing ratio 1.5 mg/mL:1.5 mg/mL), and a Cm(F)-Ela/Col mixed solution (mixing ratio 1.5 mg/mL:1.5 mg/mL).

FIG. 6 shows turbidity curves of solutions of Col on their own. FIG. 7 shows turbidity curves of a mixed solution of Col and Ela and mixed solutions of Col and three types of Cm-Ela. The turbidity curve of the Ela and Col mixed solution had the same shape as that of Col on its own, but the turbidity intensity was less than that of Col on its own. It is thought from the above that in the case of non-modified Ela, the Ela molecule was taken into Col in an non-self-assembled state because of the gelling property of Col taking in molecules therearound when starting self assembly. The decrease in turbidity intensity is thought to be due to Col taking in un-self-assembled Ela molecules rather than gelling of Col on its own. In the mixed solutions of Col and three types of Cm-Ela, the temperature at which self assembly thereof started was similar to the temperature at which self assembly of each of the three types of Cm-Ela on its own started, but the turbidity intensity increased. It is thought that since the temperature at which self assembly of the mixed solution of Cm-Ela and Col started was lower than the temperature (gelling temperature) at which self assembly of Col on its own started, self assembly of Cm-Ela had a large effect when self assembly of Col started.

(Tensile Test)

Opposite ends of a mixed gel of Ela and Col and a mixed gel of Cm-Ela and Col were fixed in a screw type material tester (Autograph AG-S-J, Shimadzu Corporation) so that the initial lengths thereof were 5 mm, the thickness and width of each gel were measured, and cross-sectional areas were obtained. Subsequently, the relationship between stress and strain when each gel was stretched only by 3 mm (strain 60%) at a displacement speed of 0.05 mm/s was obtained. Furthermore, each gel was stretched at a displacement speed of 0.05 mm/s until breakage, breaking stress was measured, and the relationship between stress and strain when stretched until breakage was obtained.

Figure 8:
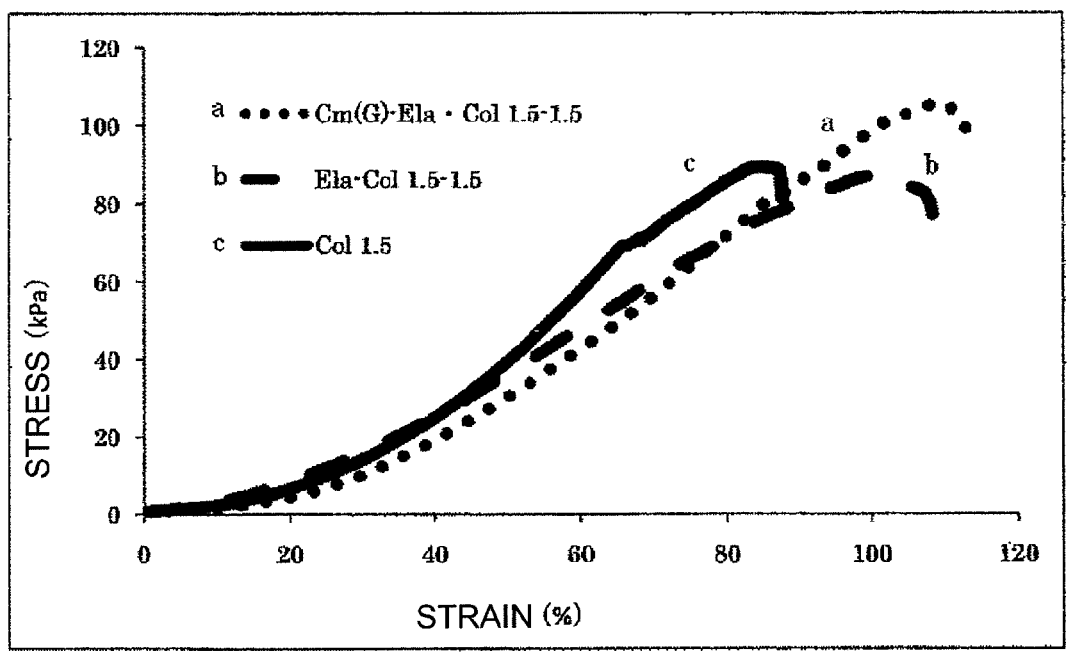
FIG. 8 is a stress-strain curves of a Col single gel (1.5 mg/mL), an Ela/Col mixed gel (mixing ratio 1.5 mg/mL:1.5 mg/mL), and a Cm(G)-Ela/Col mixed gel (mixing ratio 1.5 mg/mL:1.5 mg/mL).

Stress-strain curves of the gel of Col on its own, the mixed gel of Ela and Col, and the mixed gel of Cm(G)-Ela and Col are shown in FIG. 8. It can be seen from FIG. 8 that the breaking stress of the gel of Col on its own was 89 kPa and the maximum strain was 84%. The breaking stress of the Ela/Col mixed gel was 87 kPa and the maximum strain was 101%, the breaking stress being the same level as that of the gel of Col on its own, and the maximum strain being larger than the gel of Col on its own. Furthermore, the breaking stress of the Cm(G)-Ela/Col mixed gel was 106 kPa and the maximum strain was 109%, both the breaking stress and the maximum strain being larger than those of the Ela/Col mixed gel. From these results, it is surmised that adding Ela to Col will impart resilience to the gel, and adding Cm(G)-Ela, which has a high self-assembling ability, will impart rigidity and yet higher resilience.

Figure 9:
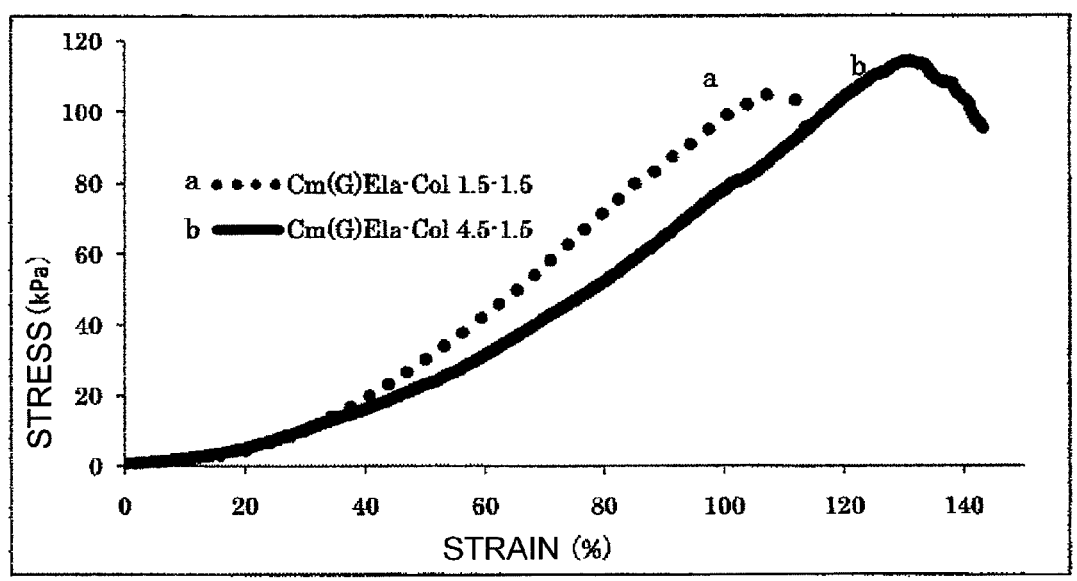
FIG. 9 is a stress-strain curves of Cm(G)-Ela/Col mixed gel (mixing ratio 1.5 mg/mL:1.5 mg/mL) and Cm(G)-Ela/Col mixed gel (mixing ratio 4.5 mg/mL:1.5 mg/mL) having different mixing ratios of Cm(G)-Ela relative to Col.

Stress-strain curves of the mixed gel of Cm(G)-Ela and Col when the mixing ratio of Cm(G)-Ela to Col was changed are shown in FIG. 9. From FIG. 9, compared with a breaking stress of 106 kPa and a maximum strain of 109% of the Cm(G)-Ela/Col mixed gel (mixing ratio 1.5 mg/mL:1.5 mg/mL), the breaking stress of the Cm(G)-Ela/Col mixed gel (mixing ratio 4.5 mg/mL:1.5 mg/mL) was 114 kPa, the maximum strain was 130%, and both the breaking stress and the maximum strain increased. It is thought that increasing the amount of Cm(G)-Ela added imparted greater resilience and rigidity. Furthermore, it would appear that since the percentage increase (20%) for the maximum strain was larger than the percentage increase (8%) for the breaking stress, there was larger contribution to improvement of resilience than rigidity from Ela.

Figure 10:
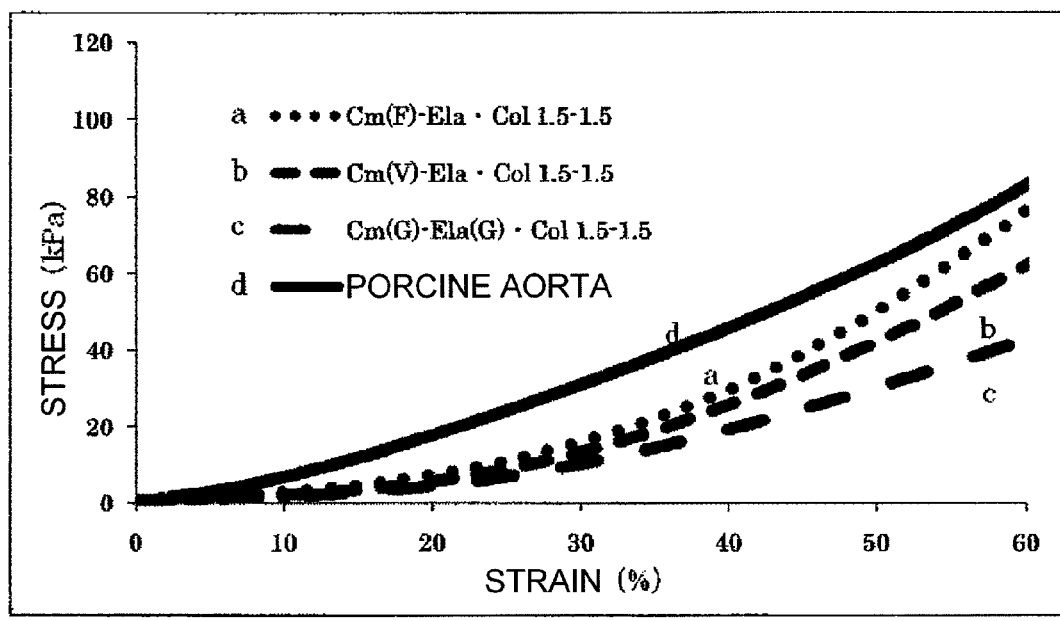
FIG. 10 is a stress-strain curves in which three different types of mixed gels, that is, Cm(G)-Ela/Col mixed gel (mixing ratio 1.5 mg/mL:1.5 mg/mL), Cm(V)-Ela/Col mixed gel (mixing ratio 1.5 mg/mL:1.5 mg/mL), and Cm(F)-Ela/Col mixed gel (mixing ratio 1.5 mg/mL:1.5 mg/mL), and porcine aorta are compared in terms of stress and strain up to a strain of 60%.

Stress-strain curves of the mixed gel of Cm(G)-Ela and Col, the mixed gel of Cm(V)-Ela and Col, the mixed gel of Cm(F)-Ela and Col, and porcine aorta are shown in FIG. 10. From FIG. 10, the stress relative to 60% strain was 43 kPa for the Cm(G)-Ela/Col mixed gel (mixing ratio 1.5 mg/mL:1.5 mg/mL), 63 kPa for the Cm(V)-Ela/Col mixed gel (mixing ratio 1.5 mg/mL:1.5 mg/mL), and 78 kPa for the Cm(F)-Ela/Col mixed gel (mixing ratio 1.5 mg/mL:1.5 mg/mL). That is, the stress was larger for the mixed gel of collagen and the chemically modified water-soluble elastin that was coupled with an amino acid methyl ester having high hydrophobicity. From the above, it is thought that the degree of contribution to improvement of stress in a mixed gel of Ela depends on the degree of the self assembly ability of Ela.

Table 1 shows the values of the stress relative to 50% strain of three types of the chemically modified water-soluble elastin/collagen mixed gel of the present invention, that is, the Cm(G)-Ela/Col mixed gel (mixing ratio 1.5 mg/mL:1.5 mg/mL), the Cm(V)-Ela/Col mixed gel (mixing ratio 1.5 mg/mL:1.5 mg/mL), and the Cm(F)-Ela/Col mixed gel (mixing ratio 1.5 mg/mL:1.5 mg/mL), and a 15 kGy γ ray-irradiated Cm(G)-Ela/Col mixed gel (mixing ratio 1.5 mg/mL:1.5 mg/mL) and a 30 kGy γ ray-irradiated Cm(G)-Ela/Col mixed gel (mixing ratio 1.5 mg/mL:1.5 mg/mL) formed by irradiating the Cm(G)-Ela/Col mixed gel with 15 kGy and 30 kGy of γ rays, when compared with those of porcine aorta and canine abdominal aorta.

TABLE 1

| Sample | Stress (kPa) |
|---|---|
| Cm(G)-Ela/Col mixed gel (mixing ratio 1.5 mg/ml:1.5 mg/ml) | 29 |
| Cm(V)-Ela/Col mixed gel (mixing ratio 1.5 mg/ml:1.5 mg/ml) | 42 |
| Cm(F)-Ela/Col mixed gel (mixing ratio 1.5 mg/ml:1.5 mg/ml) | 51 |
| 15 kGy γ-irradiated Cm(G)-Ela/Col mixed gel (mixing ratio 1.5 mg/ml:1.5 mg/ml) | 130 |
| 30 kGy γ-irradiated Cm(G)-Ela/Col mixed gel (mixing ratio 1.5 mg/ml:1.5 mg/ml) | 219 |
| Porcine aorta | 62 |
| Canine abdominal aorta | 62 |

From Table 1, the stress relative to 50% strain of the Cm(F)-Ela/Col mixed gel, which is a mixed gel of a collagen and a chemically modified water-soluble elastin formed by coupling with an amino acid methyl ester having high hydrophobicity, showed a strength close to the stress of porcine aorta and canine abdominal aorta. Furthermore, the stress of the γ ray-irradiated Cm(G)-Ela/Col mixed gel showed a strength larger than the stress of porcine aorta and canine abdominal aorta. This suggests the possibility of full use of the mixed gel and the γ ray-irradiated mixed gel of the present invention as a human blood vessel since they showed strength, resilience, and extensibility equal to or higher than those of the blood vessel of the body tissue.

It is also suggested that there is a possibility of obtaining a material for an artificial blood vessel having yet higher strength by increasing the amount of chemically modified water-soluble elastin added or by preparing a chemically modified water-soluble elastin by coupling with an alkyl ester of a peptide (for example, F-F, F-F-F) having higher hydrophobicity than an amino acid, and preparing a mixed gel with collagen.

(TEM Observation)

When preparing a grid, carbon at about 200 Å thick was vapor-deposited on a grid treated with 2% collodion using a Super High Clean Vacuum Coater SVC-700 Turbo (Sanyu Electron Co., Ltd.), and before adsorption of a sample it was treated using a Quick Coater SC-701 (Sanyu Electron Co., Ltd.) so that benzylamine was sprayed thinly as for the carbon film. A sample was prepared by thinly slicing a lyophilized gel using a razor, the slice was placed on the prepared grid as it was, and examination by TEM was carried out at a magnification of ×6400.

The results showed that Col had a molecular weight of about 300,000 but formed a Col fiber having a three-dimensional net structure when gelled. A state was observed in which Cm-Ela having a molecular weight of about 200,000 entered between the Col fibers and self-assembled so as to tangle with the collagen fiber, thereby forming a stronger structure.

(Preparation of Artificial Blood Vessel)

Figure 11:
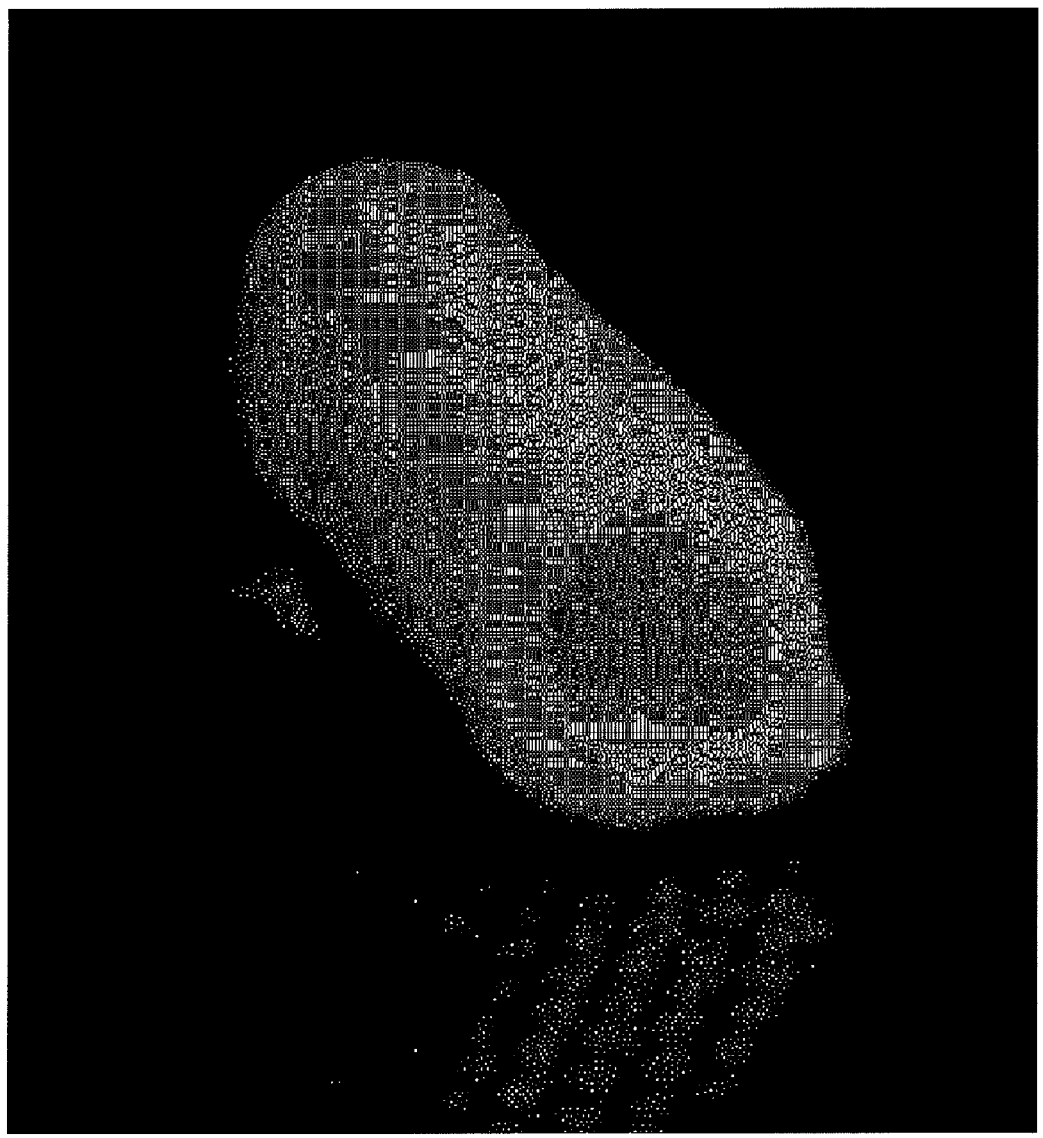
FIG. 11 is an artificial blood vessel having an inner diameter of 5 mm and an outer diameter of 8 mm prepared from a Cm(G)-Ela/Col mixed gel (mixing ratio 1.5 mg/mL:1.5 mg/mL).

A Cm(G)-Ela/Col mixed solution (mixing ratio 1.5 mg/mL:1.5 mg/mL) prepared at low temperature using PBS (pH 7.4) was poured into an 8 mm diameter tube, and a center rod having a diameter of 5 mm was subsequently inserted thereinto, thus forming a tube from the mixed solution between the diameter of 8 mm and the diameter of 5 mm. Subsequently, the mixed solution was gelled by allowing it to stand at 37° C. for about 1 hour, dried at 37° C., then allowed to stand for 48 hours with added PBS to thus be swollen, and was formed into an artificial blood vessel by pulling out the center rod (FIG. 11).

(Irradiation of Chemically Modified Water-Soluble Elastin/Collagen Mixed Gel with Radiation)

The Ela/Col mixed solution (mixing ratio 1.5 mg/mL:1.5 mg/mL) and the Cm(G)-Ela/Col mixed solution (mixing ratio 1.5 mg/mL:1.5 mg/mL) were gelled at 37° C. for 1 hour, lyophilized, and swollen for 48 hours by adding 2 mL of PBS. Subsequently, irradiation with γ rays was carried out with irradiation intensities of 15 kGy and 30 kGy at an irradiation temperature of 40° C. to 50° C. Irradiated chemically modified water-soluble elastin/collagen mixed gels of the present invention were thus obtained.

(Tensile Test of Irradiated Chemically Modified Water-Soluble Elastin/Collagen Mixed Gel of the Present Invention)

The irradiated mixed gels obtained above were fixed in a screw type material tester (Autograph AG-S-J, Shimadzu Corporation) so that the initial length was 5 mm. The thickness and the width of the gels were measured, and the cross-sectional area was determined. The relationship between stress and strain when the mixed gel was stretched at a displacement speed of 0.05 mm/s was obtained, and the relationship between stress and strain when it was stretched by only 2.5 mm (strain 50%) was obtained. Furthermore, breaking stress was measured by stretching each gel at a displacement speed of 0.05 mm/s until breakage, and the relationship between stress and strain when stretched until breakage was obtained.

Figure 12:
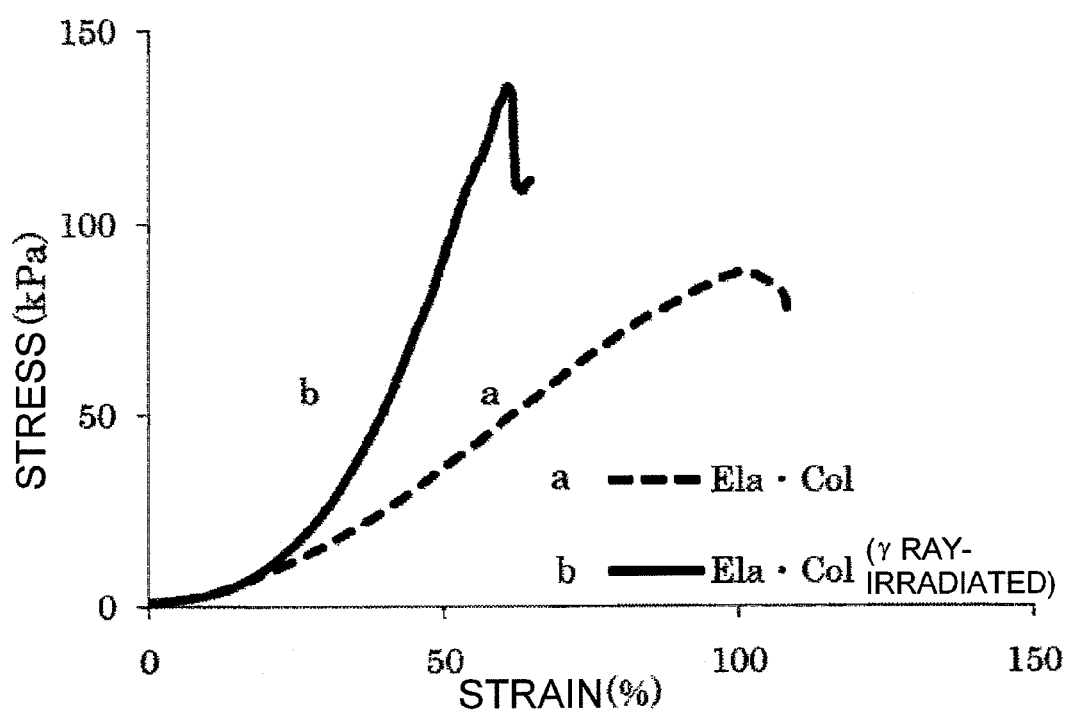
FIG. 12 is a stress-strain curves of an Ela/Col mixed gel (mixing ratio 1.5 mg/mL:1.5 mg/mL) and a γ ray-irradiated Ela/Col mixed gel (mixing ratio 1.5 mg/mL:1.5 mg/mL).
Figure 13:
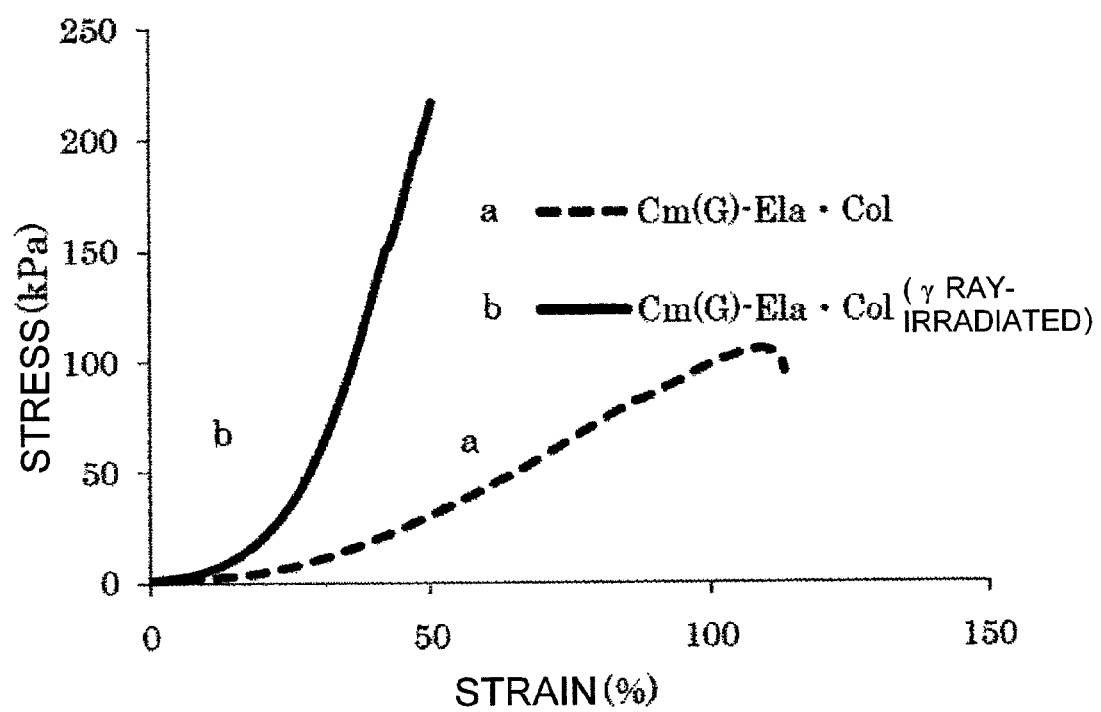
FIG. 13 is a stress-strain curves of a Cm(G)-Ela/Col mixed gel (mixing ratio 1.5 mg/mL:1.5 mg/mL) and a γ ray-irradiated Cm(G)-Ela/Col mixed gel (mixing ratio 1.5 mg/mL:1.5 mg/mL).

In order to compare non-irradiation and irradiation with γ rays, stress-strain curves of the Ela/Col mixed gel and a γ ray-irradiated Ela/Col mixed gel are shown in FIG. 12. The γ ray-irradiated Ela/Col mixed gel showed a larger breaking strength than the non-irradiated Ela/Col mixed gel. Stress-strain curves of the Cm(G)-Ela/Col mixed gel and the γ ray-irradiated Cm(G)-Ela/Col mixed gel are shown in FIG. 13. The breaking strength of the γ ray-irradiated Cm(G)-Ela/Col mixed gel was larger than the non-irradiated Cm(G)-Ela/Col mixed gel and was also larger than the γ ray-irradiated Ela/Col mixed gel (ref. FIG. 12).

Figure 14:
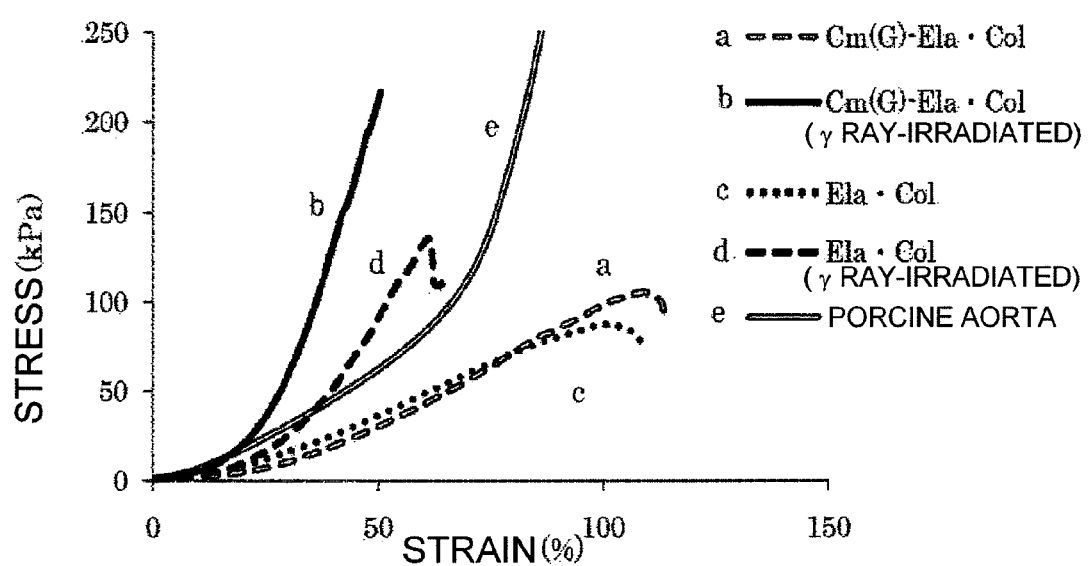
FIG. 14 is a stress-strain curves in which an Ela/Col mixed gel (mixing ratio 1.5 mg/mL:1.5 mg/mL), a γ ray-irradiated Ela/Col mixed gel (mixing ratio 1.5 mg/mL:1.5 mg/mL), a Cm(G)-Ela/Col mixed gel (mixing ratio 1.5 mg/mL:1.5 mg/mL), a γ ray-irradiated Cm(G)-Ela/Col mixed gel (mixing ratio 1.5 mg/mL:1.5 mg/mL), and porcine aorta are compared in terms of stress and strain.
Figure 15:
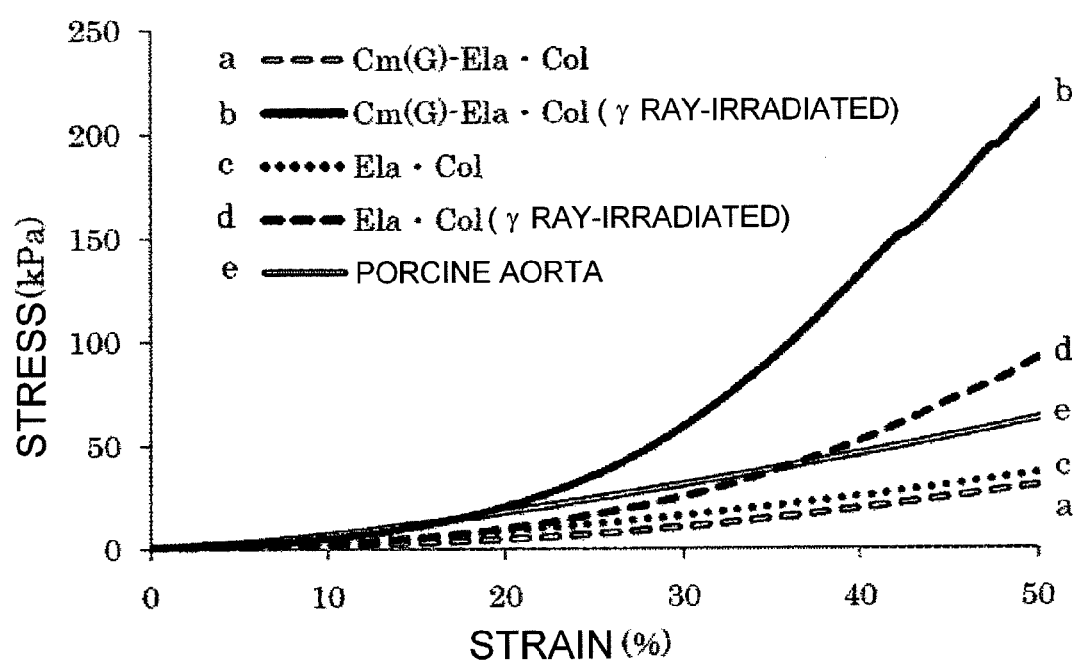
FIG. 15 is a stress-strain curves in which an Ela/Col mixed gel (mixing ratio 1.5 mg/mL:1.5 mg/mL), a γ ray-irradiated Ela/Col mixed gel (mixing ratio 1.5 mg/mL:1.5 mg/mL), a Cm(G)-Ela/Col mixed gel (mixing ratio 1.5 mg/mL:1.5 mg/mL), a γ ray-irradiated Cm(G)-Ela/Col mixed gel (mixing ratio 1.5 mg/mL:1.5 mg/mL), and porcine aorta are compared in terms of stress and strain up to a strain of 50%.

Stress-strain curves of the Ela/Col mixed gel, the γ ray-irradiated Ela/Col mixed gel, the Cm(G)-Ela/Col mixed gel, the γ ray-irradiated Cm(G)-Ela/Cot mixed gel, and porcine aorta are shown in FIG. 14, and the stress-strain curves up to a strain of 50% are shown in FIG. 15.

As is clear from FIG. 12, the maximum stress of the γ ray-irradiated Ela/Col mixed gel was about 1.5 times that of the Ela/Col mixed gel, and the maximum strain was about 0.5 times (FIG. 12). The maximum stress of the γ ray-irradiated Cm(G)-Ela/Col mixed gel relative to that of the Cm(G)-Ela/Col mixed gel was so high that the limit for the measurement equipment was exceeded (FIG. 13). It is thought that this is due to the mixed gel being crosslinked by irradiation with γ rays. Furthermore, since, regardless of whether or not there was irradiation with γ rays, the maximum stress of the Cm(G)-Ela/Col mixed gel was higher than that of the Ela/Col mixed gel, it is thought that the self assembly ability of Ela contributes to the strength of the mixed gel. When the stress-strain curves of the mixed gels and that of porcine aorta were actually compared, the γ ray-irradiated Cm(G)-Ela/Col mixed gel had a larger strength than that of porcine aorta (FIG. 14 and FIG. 15).

The result was that the maximum strain of the γ ray-irradiated Ela/Col mixed gel became small, but since the strength became large, the strain of the γ ray-irradiated Ela/Col gel is sufficient as a material. Furthermore, since the γ ray-irradiated Cm(G)-Ela/Col mixed gel gave a value beyond the limit of the measurement equipment, the strength increased to the extent that the maximum stress and the maximum strain could not be measured. This suggests that irradiation with γ rays is useful means for preparing a material for an artificial blood vessel, and the γ ray-irradiated mixed gel can be used as a material for an artificial blood vessel.

INDUSTRIAL APPLICABILITY

The chemically modified water-soluble elastin/collagen mixed gel of the present invention can be used as an artificial blood vessel in place of a human blood vessel, and can be used in treatment of a cardiovascular disease such as arteriosclerosis or aneurysm. Furthermore, it can be applied to artificial ligaments, artificial tendons, artificial skin, artificial alveoli, an artificial uterus, etc. Moreover, it can be applied to cosmetic surgery involving embedding it in the skin for removing wrinkles, etc.

Furthermore, the chemically modified water-soluble elastin/collagen mixed gel of the present invention is also useful as an artificial tissue in which the mixed gel is seeded with epithelial cells, endothelial cells, fibroblasts, smooth muscle cells, chondrocytes, etc.

Moreover, the chemically modified water-soluble elastin/collagen mixed gel of the present invention is also useful as an artificial tissue in which a growth factor such as an epidermal growth factor, a fibroblast growth factor, an insulin-like growth factor, a vascular endothelial growth factor, a transforming growth factor, or a platelet-derived growth factor, a glycosaminoglycan such as chondroitin sulfate, dermatan sulfate, heparan sulfate, keratan sulfate, heparin, or hyaluronic acid, or a cell-adhesion protein such as fibronectin, laminin, vitronectin, tenascin, thrombospondin, entactin, osteopontin, von Willebrand factor, or fibrinogen is added to the mixed gel.

The invention claimed is:

1. A chemically modified water-soluble elastin/collagen mixed gel comprising a collagen and a chemically modified water-soluble elastin, wherein the chemically modified water-soluble elastin comprises:
    an N-acylated primary or secondary amino group in a molecule of the water-soluble elastin, wherein the water-soluble elastin is a high molecular weight water-soluble elastin, and
    an amido group formed by coupling an amino group of an amino acid alkyl ester and a carboxyl group in the molecule of the high molecular weight water-soluble elastin.

2. The chemically modified water-soluble elastin/collagen mixed gel according to claim 1, wherein the weight ratio of the chemically modified water-soluble elastin to the collagen is 1:200 to 200:1.

3. The chemically modified water-soluble elastin/collagen mixed gel according to claim 1, wherein the weight ratio of the chemically modified water-soluble elastin to the collagen is 95:100 to 105:100.

4. The chemically modified water-soluble elastin/collagen mixed gel according to claim 1, wherein the chemically modified water-soluble elastin/collagen mixed gel is irradiated with radiation.

5. A process for producing a chemically modified water-soluble elastin/collagen mixed gel, the process comprising:
    (1) N-acylating some or all primary amino groups and secondary amino groups contained in a molecule of the water-soluble elastin, wherein the water-soluble elastin is a high molecular weight water-soluble elastin,
    (2) coupling some or all carboxyl groups contained in the molecule of the high molecular weight water-soluble elastin with an amino group of an amino acid lower alkyl ester, and
    (3) preparing a mixed gel by mixing in a solution state the chemically modified water-soluble elastin obtained via steps (1) and (2) with a collagen.

6. The process for producing the chemically modified water-soluble elastin/collagen mixed gel according to claim 5, wherein the weight ratio of the chemically modified water-soluble elastin to the collagen is 1:200 to 200:1.

7. The process for producing the chemically modified water-soluble elastin/collagen mixed gel according to claim 5, wherein the weight ratio of the chemically modified water-soluble elastin to and the collagen is 95:100 to 105:100.

8. A process for producing a chemically modified water-soluble elastin/collagen mixed gel, the process comprising:
    (1) N-acylating some or all primary amino groups and secondary amino groups contained in a molecule of the water-soluble elastin, wherein the water-soluble elastin is a high molecular weight water-soluble elastin, (2) coupling some or all carboxyl groups contained in the molecule of the high molecular weight water-soluble elastin with an amino group of an amino acid lower alkyl ester, (3) preparing a mixed gel by mixing in a solution state the chemically modified water-soluble elastin obtained via steps (1) and (2) with a collagen, and (4) irradiating the mixed gel obtained in (3) with radiation.

9. The process for producing the chemically modified water-soluble elastin/collagen mixed gel according to claim 8, wherein the weight ratio of the chemically modified water-soluble elastin to the collagen is 95:100 to 105:100.

10. The process for producing the chemically modified water-soluble elastin/collagen mixed gel according to claim 8, wherein the chemically modified water-soluble elastin is mixed with collagen in a ratio of 1/200 to 200/1 and irradiated with radiation.

11. A medical material comprising the chemically modified water-soluble elastin/collagen mixed gel according to claim 1.

12. An artificial blood vessel material comprising the chemically modified water-soluble elastin/collagen mixed gel according to claim 1.

13. The chemically modified water-soluble elastin/collagen mixed gel according to claim 1, wherein the N-acylated primary or secondary amino group is at least one member selected from the group consisting of: an N-formylated primary or secondary amino group, an N-acetylated primary or secondary amino group, and an N-benzolyated primary or secondary amino group.

14. The chemically modified water-soluble elastin/collagen mixed gel according to claim 1, wherein the amino acid alkyl ester is a lower alkyl ester comprising 1 to 4 carbons.

* * * * *